(12) United States Patent
Tsunomori et al.

(10) Patent No.: US 10,149,658 B2
(45) Date of Patent: Dec. 11, 2018

(54) DYNAMIC ANALYSIS SYSTEM AND ANALYSIS DEVICE

(71) Applicant: Konica Minolta, Inc., Tokyo (JP)

(72) Inventors: Akinori Tsunomori, Kodaira (JP); Yasuhiro Saiki, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 15/497,977

(22) Filed: Apr. 26, 2017

(65) Prior Publication Data

US 2017/0325771 A1 Nov. 16, 2017

(30) Foreign Application Priority Data

May 13, 2016 (JP) .................. 2016-096646

(51) Int. Cl.
*A61B 6/00* (2006.01)
*G06T 7/00* (2017.01)
*A61B 5/00* (2006.01)
*A61B 5/08* (2006.01)
*A61B 5/11* (2006.01)
(Continued)

(52) U.S. Cl.
CPC ............ *A61B 6/5217* (2013.01); *A61B 5/004* (2013.01); *A61B 5/08* (2013.01); *A61B 5/1135* (2013.01); *A61B 5/725* (2013.01); *A61B 6/463* (2013.01); *A61B 6/50* (2013.01); *G06T 7/00* (2013.01); *G06T 7/0012* (2013.01); *A61B 5/113* (2013.01); *A61B 5/1128* (2013.01); *A61B 6/465* (2013.01); *A61B 2576/02* (2013.01); *G06T 7/11* (2017.01); *G06T 2207/10116* (2013.01); *G06T 2207/30061* (2013.01); *G06T 2207/30104* (2013.01)

(58) Field of Classification Search
USPC ................................................ 382/128, 132
See application file for complete search history.

(56) References Cited

U.S. PATENT DOCUMENTS 6,915,151 B2 * 7/2005 Baumgardner .... G01R 33/5601
                                                    324/307
9,750,427 B2 * 9/2017 Prisk ...................... A61B 5/055
(Continued)

OTHER PUBLICATIONS

Rie Tanaka, et al; Ventilation-perfusion study in a ventilation-perfusion mismatch case using dynamic chest radiography; Medical Imaging and Information Sciences; vol. 26 (2009), No. 3, pp. 68-72.

*Primary Examiner* — Ishrat I Sherali
(74) *Attorney, Agent, or Firm* — Lucas & Mercanti, LLP

(57) ABSTRACT

A dynamic analysis system includes an imaging device and an analysis device. The imaging device performs dynamic imaging by emitting radiation to a chest part of a human body, thereby obtaining a series of frame images showing a dynamic state of the chest part. The analysis device includes a controller. The controller (i) selects a first plurality of frame images to be analyzed from the series of frame images obtained by the imaging device, (ii) calculates, based on the first plurality of frame images, a ventilation amount index value that indicates an amount of ventilation of a lung field and a perfusion amount index value that indicates an amount of perfusion of the lung field, and (iii) calculates a ratio of the ventilation amount index value to the perfusion amount index value.

14 Claims, 10 Drawing Sheets

(51) Int. Cl.
 *A61B 5/113* (2006.01)
 *G06T 7/11* (2017.01)

(56) References Cited

U.S. PATENT DOCUMENTS

2018/0049712 A1\* 2/2018 Muraoka ................. A61B 6/50
2018/0064830 A1\* 3/2018 Uber, III ............ A61K 49/0447

\* cited by examiner

SMALL ▨▨▨ ▧▧▧ LARGE
↑
DEFAULT NORMAL VALUE

SMALL ▨▨▨ ▧▧▧ LARGE
↑
DEFAULT NORMAL VALUE

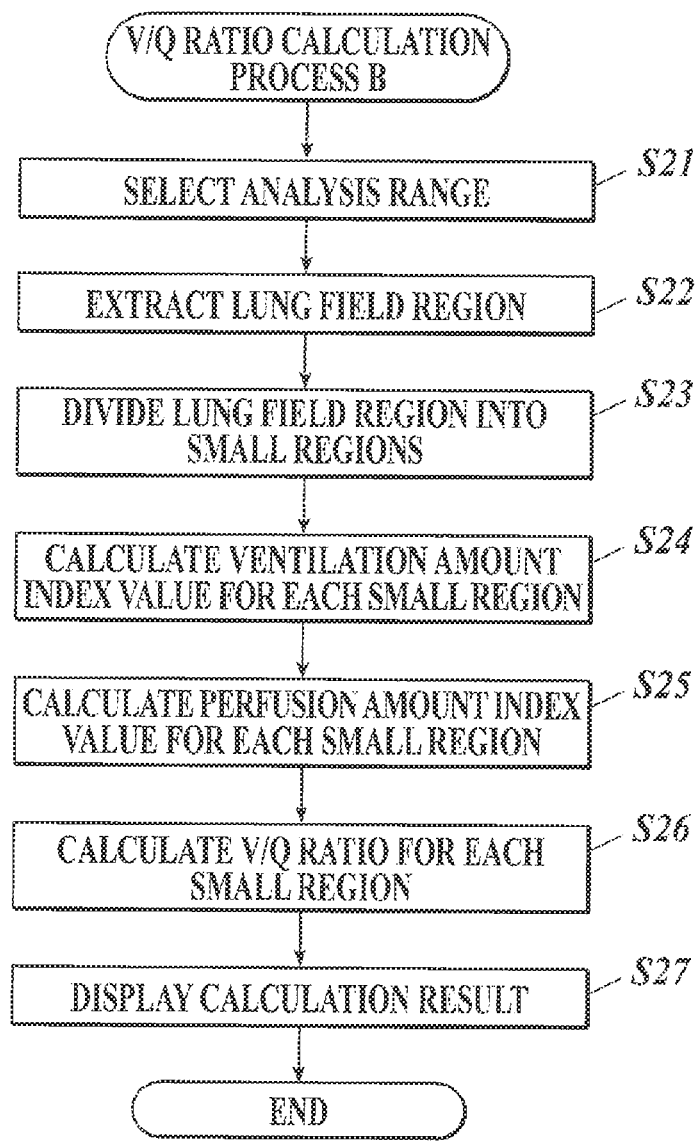

DYNAMIC ANALYSIS SYSTEM AND ANALYSIS DEVICE

CROSS-REFERENCE TO RELATED APPLICATIONS

This application is based upon and claims the benefit of priority under the Paris Convention of Japanese Patent Application No. 2016-096646 filed on May 13, 2016, the entire disclosure of which, including the specification, claims, drawings and abstract, is incorporated herein by reference in its entirety.

BACKGROUND OF THE INVENTION

1. Field of the Invention

The present invention relates to a dynamic analysis system and an analysis device.

2. Description of the Related Art

Functions of the lungs are ventilation and perfusion (blood flow). Ventilation is a function to take oxygen into the body as inhaled air and send the same to the pulmonary alveoli, and emit carbon dioxide from the pulmonary alveoli to the outside of the body as exhaled air. Perfusion is a function to send, to the pulmonary alveoli, blood which contains carbon dioxide emitted from the cells of the whole body, and send out, to the heart, blood which oxygen has entered by gas exchange in the pulmonary alveoli. That is, it is important for gas exchange that ventilation and perfusion function in a well-balanced manner. If one or both of the functions deteriorates, gas exchange does not work well.

The relationship between ventilation (V) and perfusion (Q) is important for pathophysiologically understanding respiratory diseases and is clinically evaluated by the following V/Q ratio.

$$V/Q \text{ Ratio} = \text{Amount of Ventilation } (V)/\text{Amount of Perfusion } (Q)$$

In general, the amount of ventilation of about 4 L, the amount of perfusion of about 5 L, and the V/Q ratio of about 0.8 are considered to be normal. However, if imaging is performed with a patient (examinee or subject M) standing, due to influence of gravity, the amount of ventilation is more than the above value at the upper part of the lung fields (right and left lung fields), and the amount of perfusion is more than the above value at the lower part of the lung fields.

Conventionally, the V/Q ratio is examined by ventilation scintigraphy and perfusion scintigraphy. However, they require patients to take in radioisotopes and therefore put a great strain on the patients, and also their examination time is long.

Meanwhile, there is proposed a method of calculating a ventilation change amount from frame images taken during breathing of a dynamic chest image, calculating a perfusion change amount from frame images taken during breath-holding of the dynamic chest image, and obtaining the V/Q ratio by obtaining the ratio of the change amounts (e.g., Non-Patent Document 1: Rie TANAKA, Masaki FUJIMURA, Masahide YASUI, Shigeru SANADA, Norio HAYASHI, Hiroyuki OKAMOTO, Shiro TSUJI, Yuko NANBU, and Osamu MATSUI, "Ventilation-perfusion study in a ventilation-perfusion mismatch case using dynamic chest radiography", Medical Imaging and Information Sciences, Vol. 26 (2009), No. 3, pp. 68-72). Calculating the V/Q ratio from a dynamic chest image is preferable because it puts a smaller strain on patients than examining the V/Q ratio by ventilation scintigraphy and perfusion scintigraphy, and also its examination time is short.

However, in the method described in Non-Patent Document 1, the V/Q ratio is calculated from the analysis results of frame images taken at different timings. Therefore, the V/Q ratio cannot be calculated with high accuracy.

BRIEF SUMMARY OF THE INVENTION

Objects of the present invention include calculating the V/Q ratio with high accuracy by using a dynamic chest image.

In order to achieve the above and/or other objects, according to a first aspect of the present invention, there is provided a dynamic analysis system including: an imaging device which performs dynamic imaging by emitting radiation to a chest part of a human body, thereby obtaining a series of frame images showing a dynamic state of the chest part; and an analysis device including a controller which: selects a first plurality of frame images to be analyzed from the series of frame images obtained by the imaging device; calculates, based on the first plurality of frame images, a ventilation amount index value that indicates an amount of ventilation of a lung field and a perfusion amount index value that indicates an amount of perfusion of the lung field; and calculates a ratio of the ventilation amount index value to the perfusion amount index value.

According to a second aspect of the present invention, there is provided an analysis device including a controller which: selects a plurality of frame images to be analyzed from a series of frame images showing a dynamic state of a chest part of a human body obtained by dynamic imaging performed by emitting radiation to the chest part of the human body; calculates, based on the selected plurality of frame images, a ventilation amount index value that indicates an amount of ventilation of a lung field and a perfusion amount index value that indicates an amount of perfusion of the lung field; and calculates a ratio of the ventilation amount index value to the perfusion amount index value.

BRIEF DESCRIPTION OF THE SEVERAL VIEWS OF THE DRAWING

The present invention is fully understood from the detailed description given hereinafter and the accompanying drawings, which are given byway of illustration only and thus are not intended to limit the present invention, wherein:

FIG. 10 is a flowchart of a V/Q ratio calculation process B performed by the control unit of the diagnostic console shown in FIG. 1;

DETAILED DESCRIPTION OF THE INVENTION

Hereinafter, embodiments of the present invention are described in detail with reference to the drawings. However, the scope of the present invention is not limited to the embodiments or illustrated examples.

First Embodiment

[Configuration of Dynamic Analysis System 100]

First, the configuration of a first embodiment is described.

Figure 1:
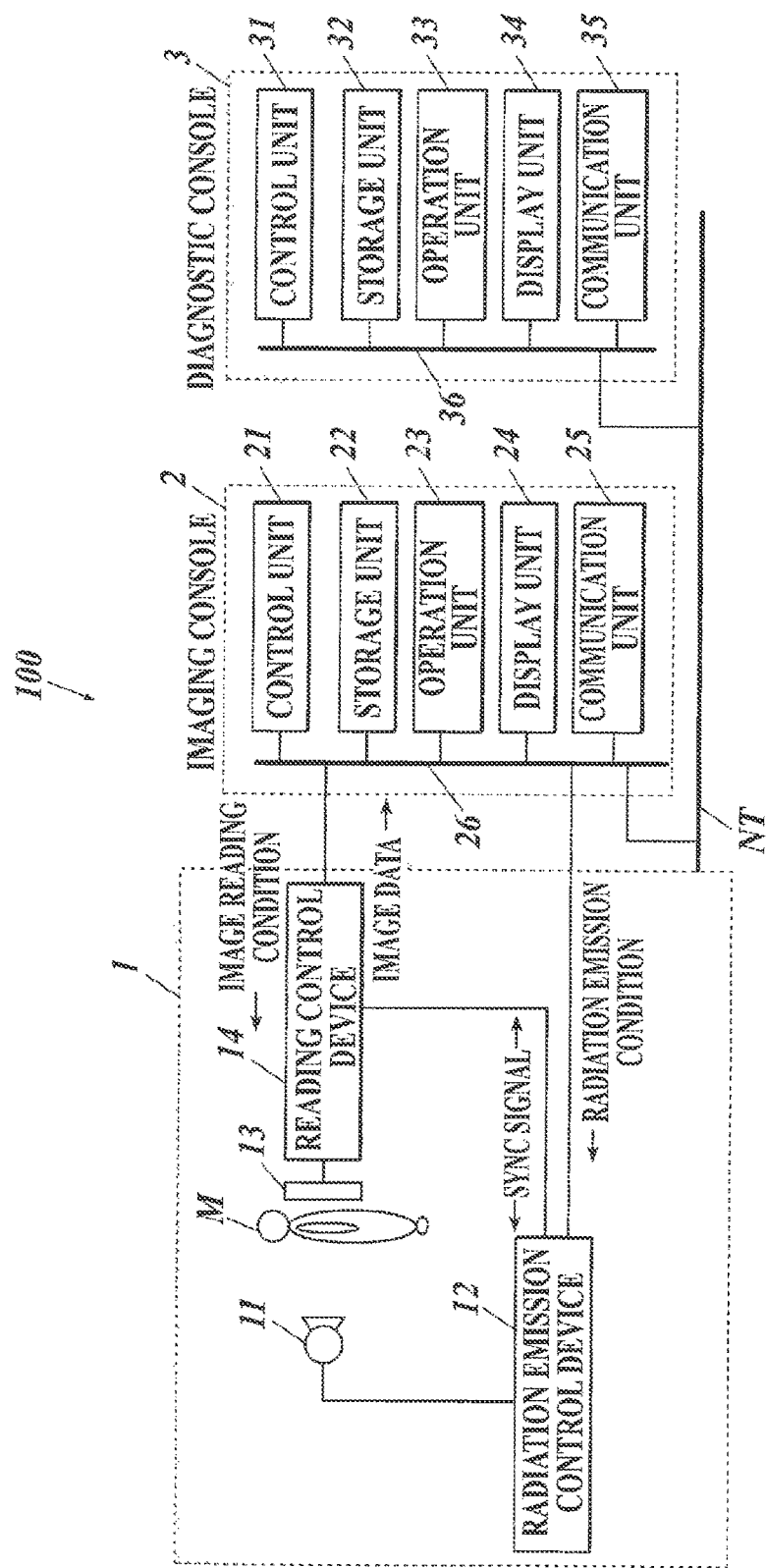
FIG. 1 shows the overall configuration of a dynamic analysis system according to embodiments of the present invention.

FIG. 1 shows the overall configuration of a dynamic analysis system 100 according to the embodiment(s) of the present invention.

As shown in FIG. 1, the dynamic analysis system 100 includes: an imaging device 1; an imaging console 2 connected with the imaging device 1 via a communication cable or the like; and a diagnostic console 3 connected with the imaging console 2 via a communication network NT, such as a LAN (Local Area Network). The devices or the like of the dynamic analysis system 100 are in conformity with DICOM (Digital Image and Communications in Medicine) standard and communicate with each other in conformity with DICOM.

[Configuration of Imaging Device 1]

The imaging device 1 is an imaging unit which images a cyclic dynamic state of a chest part. Examples of the cyclic dynamic state include: change in shape of the lungs, i.e., expansion and contraction of the lungs, accompanying respiration; and pulsation of the heart. Dynamic imaging is performed by repeatedly emitting pulsed radiation, such as X-rays, to a subject M at predetermined time intervals (pulse emission) or continuously emitting radiation without a break to a subject M at a low dose rate (continuous emission), thereby obtaining a plurality of images showing the dynamic state. A series of images obtained by dynamic imaging is called a dynamic image. Images constituting a dynamic image are called frame images. In the embodiment(s) described below, dynamic imaging is performed by pulse emission as an example.

A radiation source 11 is disposed to face a radiation detection unit 13 having a subject M in between, and emits radiation (X-rays) to the subject M under the control of a radiation emission control device 12.

The radiation emission control device 12 is connected with the imaging console 2, and controls the radiation source 11 based on radiation emission conditions input from the imaging console 2 so as to perform radiation imaging. The radiation emission conditions input from the imaging console 2 include a pulse rate, a pulse width, a pulse interval, the number of frames (frame images) to be taken by one imaging, a value of current of an X-ray tube, a value of voltage of the X-ray tube, and a type of added filter. The pulse rate is the number of times radiation is emitted per second, and matches the frame rate described below. The pulse width is a period of time for one radiation emission. The pulse interval is a period of time from the start of one radiation emission to the start of the next radiation emission, and matches the frame interval described below.

The radiation detection unit 13 is constituted of a semiconductor image sensor, such as an FPD. The FPD is constituted of detection elements (pixels) arranged at predetermined points on a substrate, such as a glass substrate, in a matrix. The detection elements detect radiation (intensity of radiation) which has been emitted from the radiation source 11 and passed through at least a subject M, convert the detected radiation into electric signals, and accumulate the electric signals therein. The pixels are provided with switching elements, such as TFTs (Thin Film Transistors). There are an indirect conversion type FPD which converts X-rays into electric signals with photoelectric conversion element(s) via scintillator(s) and a direct conversion type FPD which directly converts X-rays into electric signals. Either of them can be used.

The radiation detection unit 13 is disposed to face the radiation source 11 having a subject M in between.

A reading control device 14 is connected with the imaging console 2. The reading control device 14 controls the switching elements of the pixels of the radiation detection unit 13 based on the image reading conditions input from the imaging console 2 to switch the pixels to read the electric signals accumulated in the pixels, thereby reading the electric signals accumulated in the radiation detection unit 13 and obtaining image data. This image data is a frame image(s). The reading control device 14 outputs the obtained frame images to the imaging console 2. The image reading conditions include a frame rate, a frame interval, a pixel size and an image size (matrix size). The frame rate is the number of frame images to be obtained per second, and matches the pulse rate described above. The frame interval is a period of time from the start of one frame image obtaining action to the start of the next frame image obtaining action, and matches the pulse interval described above.

The radiation emission control device 12 and the reading control device 14 are connected with one another, and exchange sync signals so as to synchronize radiation emission actions with image reading actions.

[Configuration of Imaging Console 2]

The imaging console 2 outputs the radiation emission conditions and the image reading conditions to the imaging device 1 so as to control the radiation imaging and the radiation image reading actions performed by the imaging device 1, and also displays the dynamic image obtained by the imaging device 1 so that a radiographer, such as a radiologist, can check if positioning has no problem, and also can determine if the dynamic image is suitable for diagnosis.

The imaging console 2 includes, as shown in FIG. 1, a control unit 21, a storage unit 22, an operation unit 23, a display unit 24 and a communication unit 25. These units are connected to one another via a bus 26.

The control unit 21 includes a CPU (Central Processing Unit) and a RAM (Random Access Memory). The CPU of the control unit 21 reads a system program and various process programs stored in the storage unit 22 in response to operation on the operation unit 23, opens the read programs in the RAM, and performs various processes, such as the below-described imaging control process, in accordance with the opened programs, thereby performing concentrated control of actions of the units or the like of the imaging console 2 and the radiation emitting actions and the reading actions of the imaging device 1.

The storage unit 22 is constituted of a nonvolatile semiconductor memory, a hard disk or the like. The storage unit 22 stores therein various programs to be executed by the control unit 21, parameters necessary to perform processes of the programs, data, such as process results, and so forth. For example, the storage unit 22 stores therein a program for the imaging control process shown in FIG. 2. The storage unit 22 also stores therein the radiation emission conditions and the image reading conditions for respective imaging sites (here, the chest part). The programs are stored in the form of a computer readable program code(s), and the control unit 21 acts in accordance with the program code.

The operation unit 23 includes: a keyboard including cursor keys, number input keys and various function keys; and a pointing device, such as a mouse, and outputs, to the control unit 21, command signals input by key operation on the keyboard or by mouse operation. The operation unit 23 may have a touch panel on a display screen of the display unit 24. In this case, the operation unit 23 outputs command signals input via the touch panel to the control unit 21.

The display unit 24 is constituted of a monitor, such as an LCD (Liquid Crystal Display) or a CRT (Cathode Ray Tube), and displays thereon commands input from the operation unit 23, data and so forth in accordance with commands of display signals input from the control unit 21.

The communication unit 25 includes a LAN adapter, a modem and a TA (Terminal Adapter), and controls data exchange with devices connected to the communication network NT.

[Configuration of Diagnostic Console 3]

The diagnostic control 3 is a dynamic analysis device which obtains the dynamic image from the imaging console 2, and displays the obtained dynamic image and/or the analysis result of the dynamic image to help a doctor(s) make a diagnosis. In the embodiment(s), the diagnostic console 3 calculates the V/Q ratio based on the dynamic image of the chest part, and displays the result.

The diagnostic console 3 includes, as shown in FIG. 1, a control unit 31 (controller), a storage unit 32, an operation unit 33, a display unit 34 (display) and a communication unit 35. These units are connected to one another via a bus 36.

The control unit 31 includes a CPU and a RAM. The CPU of the control unit 31 reads a system program and various process programs stored in the storage unit 32 in response to operation on the operation unit 33, opens the read programs in the RAM, and performs various processes, such as the below-described V/Q ratio calculation process A, in accordance with the opened programs, thereby performing concentrated control of actions of the units or the like of the diagnostic console 3.

The storage unit 32 is constituted of a nonvolatile semiconductor memory, a hard disk or the like. The storage unit 32 stores therein various programs, including a program for the V/Q ratio calculation process A, to be executed by the control unit 31, parameters necessary to perform processes of the programs, data, such as process results, and so forth.

The programs are stored in the form of a computer readable program code(s), and the control unit 31 acts in accordance with the program code.

The operation unit 33 includes: a keyboard including cursor keys, number input keys and various function keys; and a pointing device, such as a mouse, and outputs, to the control unit 31, command signals input by key operation on the keyboard or by mouse operation. The operation unit 33 may have a touch panel on a display screen of the display unit 34. In this case, the operation unit 33 outputs command signals input via the touch panel to the control unit 31.

The display unit 34 is constituted of a monitor, such as an LCD or a CRT, and performs various types of display in accordance with commands of display signals input from the control unit 31.

The communication unit 35 includes a LAN adapter, a modem and a TA, and controls data exchange with devices connected to the communication network NT.

[Actions of Dynamic Analysis System 100]

Next, actions of the dynamic analysis system 100 are described.

[Actions of Imaging Device 1 and Imaging Console 2]

First, imaging actions performed by the imaging device 1 and the imaging console 2 are described.

Figure 2:
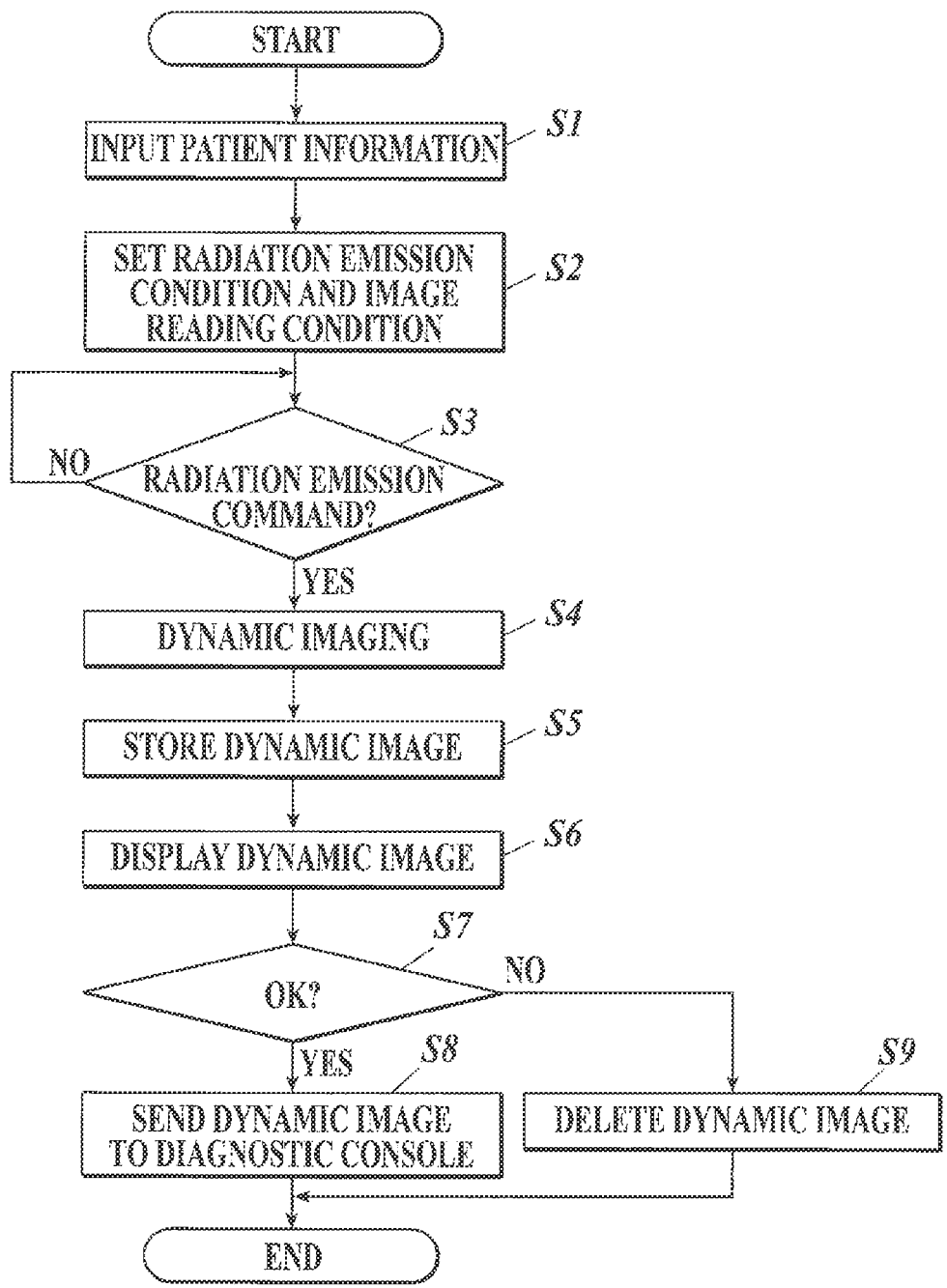
FIG. 2 is a flowchart of an imaging control process performed by a control unit of an imaging console shown in FIG. 1.

FIG. 2 shows the imaging control process performed by the control unit 21 of the imaging console 2. The imaging control process is performed by the control unit 21 in cooperation with the program stored in the storage unit 22.

First, a radiographer operates the operation unit 23 of the imaging console 2 so as to input patient information (patient name, height, weight, age, sex, etc.) on a patient, who is an imaging object (subject M), and an imaging site (here, the chest part) (Step S1).

Next, the control unit 21 reads radiation emission conditions from the storage unit 22 so as to set them in the radiation emission control device 12, and also reads image reading conditions from the storage unit 22 so as to set them in the reading control device 14 (Step S2).

Next, the control unit 21 waits for a radiation emission command to be input by radiographer operation on the operation unit 23 (Step S3). Here, the radiographer places the subject M between the radiation source 11 and the radiation detection unit 13 and performs positioning. When preparations for imaging are complete, the radiographer operates the operation unit 23 so as to input the radiation emission command.

When receiving the radiation emission command input through the operation unit 23 (Step S3; YES), the control unit 21 outputs an imaging start command to the radiation emission control device 12 and the reading control device 14 to start dynamic imaging (Step S4). That is, the radiation source 11 emits radiation at pulse intervals set in the radiation emission control device 12, and accordingly the radiation detection unit 13 obtains (generates) a series of frame images. The imaging device 1 may include a sound output unit and/or a display unit, and when the control unit 21 outputs the imaging start command, the sound output unit may output a sound and/or the display unit may display an indication of respiratory guidance, such as "breathe in", "breathe out" or "hold it". Also, when the control unit 21 outputs the imaging start command, the radiation source 11 may emit radiation at the timing of predetermined respiratory guidance (e.g., "breathe in").

When imaging for a predetermined number of frame images finishes, the control unit 21 outputs an imaging end command to the radiation emission control device 12 and the reading control device 14 to stop the imaging actions. The number of frame images to be taken covers at least one respiration cycle.

Each time a frame image is obtained by imaging, the obtained frame image is input to the imaging console 2 and stored in the storage unit 22, the frame image being correlated with a number indicating what number in the imaging order the frame image has been taken (frame number) (Step S5), and also is displayed on the display unit 24 (Step S6). The radiographer checks the positioning or the like with the displayed dynamic image, and determines whether the dynamic image obtained by dynamic imaging is suitable for diagnosis (Imaging OK) or re-imaging is necessary (Imaging NG). Then, the radiographer operates the operation unit 23 so as to input the determination result.

When the determination result "Imaging OK" is input by radiographer operation on the operation unit 23 (Step S7; YES), the control unit 21 attaches, to the respective frame images obtained by dynamic imaging (e.g., writes, in the header region of the image data in DICOM), supplementary information such as an ID to identify the dynamic image, the patient information, the imaging site, the radiation emission conditions, the image reading conditions, and the respective numbers indicating what number in the imaging order the respective frame images have been taken (frame numbers), and sends the same to the diagnostic console 3 through the communication unit 25 (Step S8), and then ends the imaging control process. If a sound(s) and/or an indication(s) of respiratory guidance have been output and/or displayed, the control unit 21 may attach, to the respective frame images, the respiratory guidance information output at the time of imaging for the respective frame images.

On the other hand, when the determination result "Imaging NG" is input by radiographer operation on the operation unit 23 (Step S7; NO), the control unit 21 deletes the frame images (the series of frame images) from the storage unit 22 (Step S9), and then ends the imaging control process. In this case, re-imaging is necessary.

[Actions of Diagnostic Console 3]

Next, actions of the diagnostic console 3 are described.

Figure 3:
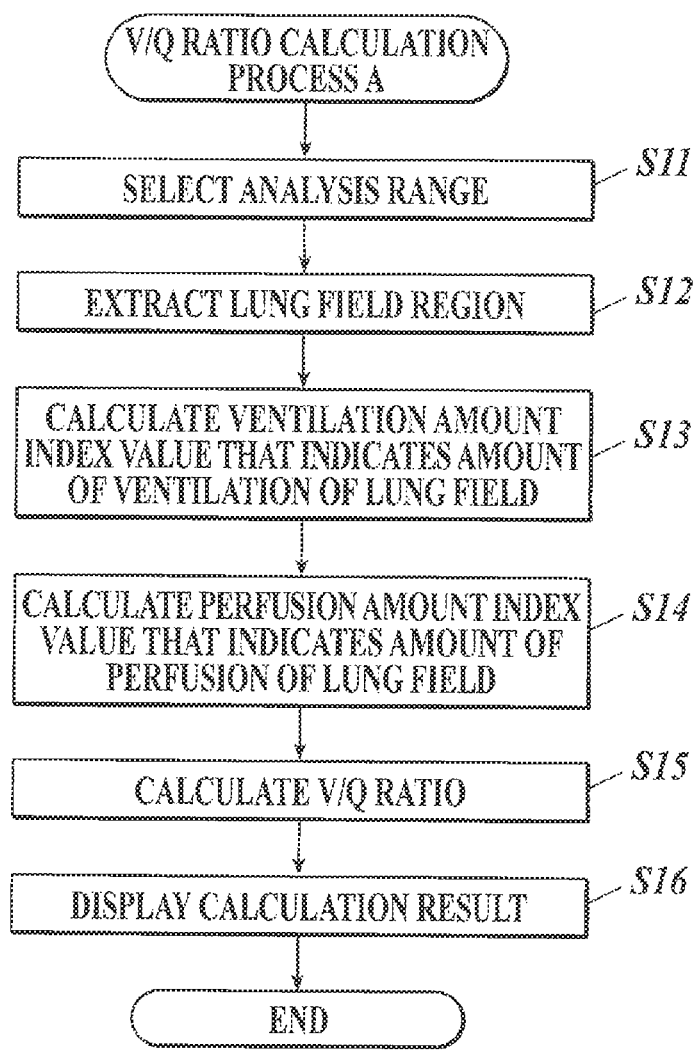
FIG. 3 is a flowchart of a V/Q ratio calculation process A performed by a control unit of a diagnostic console shown in FIG. 1.

In the diagnostic console 3, when receiving a series of frame images of a dynamic image from the imaging console 2 through the communication unit 35, the control unit 31 performs the V/Q ratio calculation process A shown in FIG. 3 in cooperation with the program stored in the storage unit 32.

Hereinafter, flow of the V/Q ratio calculation process A is described with reference to FIG. 3.

First, the control unit 31 selects an analysis range (i.e., a plurality of frame images to be analyzed) from a series of frame images of a dynamic image (Step S11).

Figure 4:
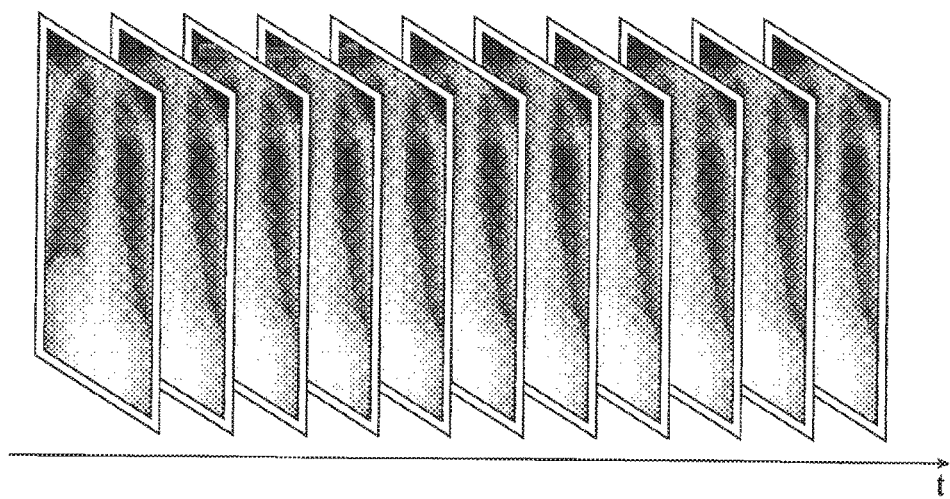
FIG. 4 is an illustration to explain an analysis range.

To calculate the V/Q ratio, ventilation analysis and perfusion analysis are performed on the dynamic image, and the ratio of the obtained ventilation amount index value that indicates the amount of ventilation of the lung fields to the obtained perfusion amount index value that indicates the amount of perfusion of the lung fields is calculated. As shown as "Example 1" in FIG. 4, a ventilation analysis range (a plurality of frame images to be analyzed as to the ventilation function) and a perfusion analysis range (a plurality of frame images to be analyzed as to the perfusion function) may coincide with each other, or as shown as "Example 2" in FIG. 4, may overlap with each other. That is, in Step S11, one analysis range may be selected as both the ventilation analysis range and the perfusion analysis range, or individual analysis ranges may be selected as the ventilation analysis range and the perfusion analysis range.

If individual analysis ranges are selected as the ventilation analysis range and the perfusion analysis range, their overlapping range (i.e., a range included in both the ventilation analysis range and the perfusion analysis range) is selected as the V/Q ratio analysis range. The analysis range(s) may be selected manually by user operation on the operation unit 33 or may be selected automatically by the control unit 31.

As a method for manually selecting the analysis range, for example, provided is a method of: displaying thumbnail images of respective frame images (a series of frame image) of a dynamic image on the display unit 34; and selecting, as the analysis range, a series of frame images (hereinafter called "a sub-series of frame images") between a start frame image and an end frame image, inclusive, both specified by user operation on the operation unit 33.

Figure 5:
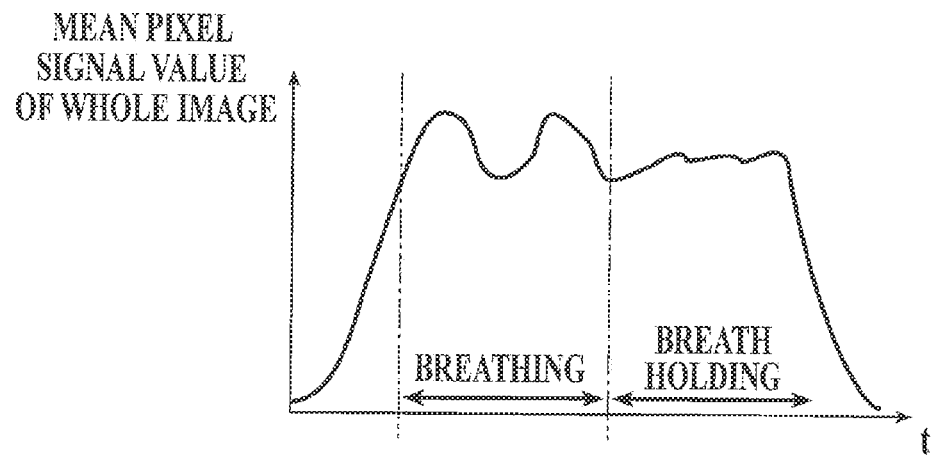
FIG. 5 is a graph of a waveform showing time change in pixel signal value of a whole frame image.

Alternatively, provided may be a method of: calculating, for each frame image of a dynamic image, the mean of pixel signal values (density values) (mean pixel signal value) of the whole image; displaying a waveform formed by plotting the calculated values on a graph having the horizontal axis representing elapsed time t from the start of imaging and the vertical axis representing the mean pixel signal value of the whole image (shown in FIG. 5, i.e., a waveform showing time change in mean pixel signal value of the whole image) on the display unit 34; and selecting, as the analysis range, a sub-series of frame images located between a start point and an end point on the displayed waveform both specified by user operation on the operation unit 33, frame images corresponding to the start point and the end point being inclusive.

Figure 6:
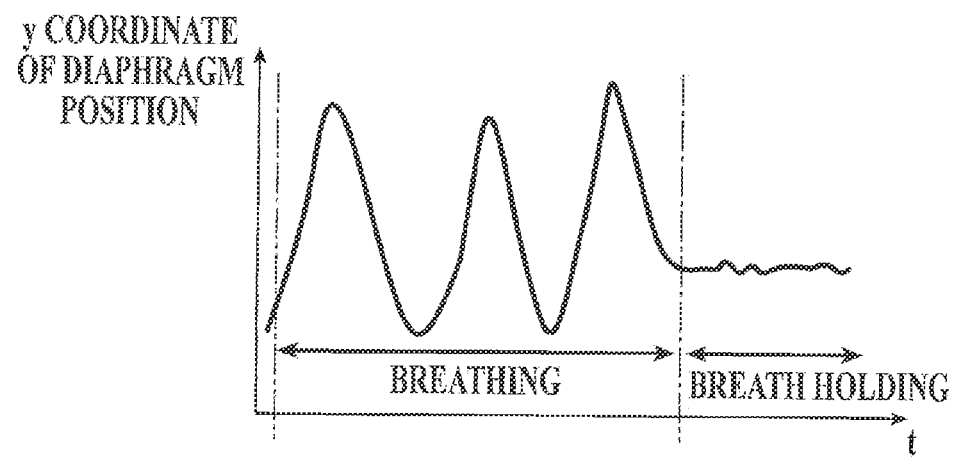
FIG. 6 shows an example of a waveform showing time change in moving amount of a diaphragm.

Alternatively, provided may be a method of: obtaining the y coordinate of the position of the diaphragm (diaphragm position) from each frame image of a dynamic image; displaying a waveform formed by plotting the obtained y coordinates of the diaphragm position on a graph having the horizontal axis representing elapsed time t from the start of imaging and the vertical axis representing the y coordinate (shown in FIG. 6, i.e., a waveform showing time change in y coordinate of the diaphragm position) on the display unit 34; and selecting, as the analysis range, a sub-series of frame images located between a start point and an end point on the displayed waveform both specified by user operation on the operation unit 33, frame images corresponding to the start point and the endpoint being inclusive. The y coordinate of the diaphragm position can be obtained, for example, by: performing a publically-known edge extraction process on each frame image, thereby extracting edges of the lung fields containing the diaphragm; searching for, among the extracted edges, edges extending somewhat along the x direction (horizontal direction) being approximately perpendicular to the moving direction of the diaphragm, from the +y side (lower side of the image) to the −y side (upper side of the image) with respect to each x coordinate; and obtaining, as the y coordinate of the diaphragm position of the frame image, the mean of y coordinates of a curve which is a set of edges (points) detected first with respect to the respective x coordinates.

As a method for automatically selecting the analysis range, for example, provided are a method of automatically selecting the analysis range based on the supplementary information and a method of automatically selecting the analysis range based on image analysis.

As the method of automatically selecting the analysis range based on the supplementary information, for example, if the supplementary information attached to each frame image of a dynamic image contains respiratory guidance information output at the time of imaging for the frame image as described above, provided is a method of selecting the analysis range based on the respiratory guidance information; for example, selecting, as the analysis range, a sub-series of frame images for which "breathe in" and "breathe out" are in succession.

Figure 7A:
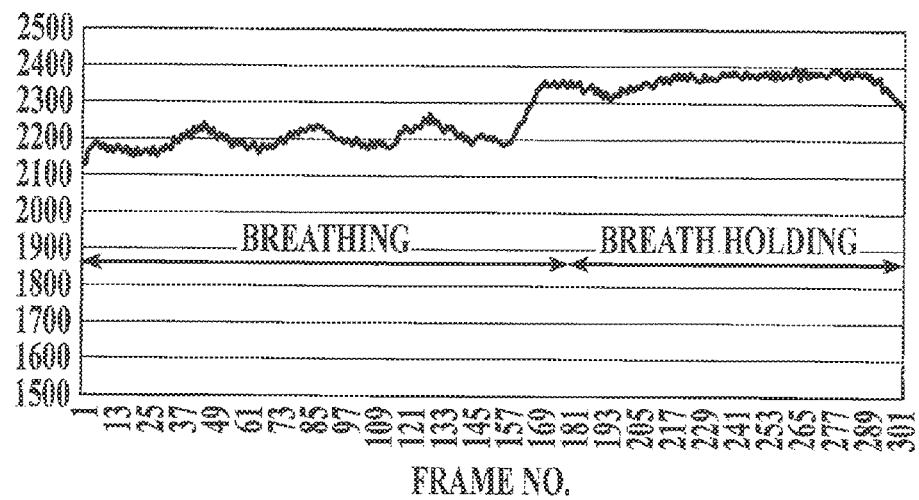
FIG. 7A is a graph of a waveform showing time change in pixel signal value of a whole frame image.
Figure 7B:
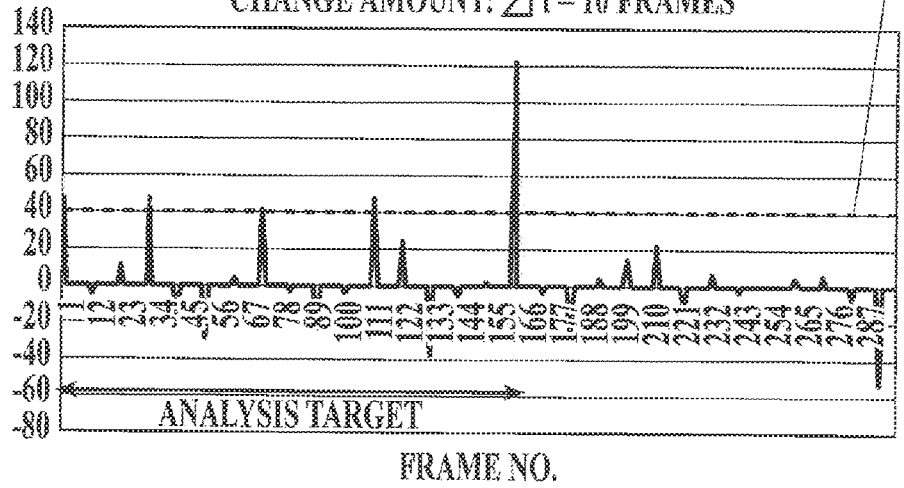
FIG. 7B is a graph showing a change amount of the pixel signal value shown in FIG. 7A at ten-frames intervals.

As the method of automatically selecting the analysis range based on image analysis, for example, provided is a method of first calculating, for each frame image of a dynamic image, the mean pixel signal value of the whole image; and calculating a difference value (change amount) in the mean pixel signal value between frame images separated by an interval of a predetermined number of frame images (e.g., 10 frame images). Here, refer to FIG. 7A. As shown in FIG. 7A, in the breathing state, the mean pixel signal value changes on the whole, whereas in the breath holding state, the mean pixel signal value does not change on the whole. Hence, the above method is advanced to: determining, as the breathing state, a range in which the difference value (frame-to-frame difference value) exceeds a predetermined threshold value again within predetermined time of the last time as shown in FIG. 7B; and selecting s sub-series of frame images in/of the range (analysis target) as the analysis range.

Next, the control unit 31 extracts lung field regions (right and left lung field regions) from each frame image of the selected analysis range (frame images) of the dynamic image (Step S12).

In Step S12, first, the lung field regions are extracted from each frame image. Any lung field region extraction method can be used. For example, a threshold value is obtained from a histogram of pixel signal values (density values) of frame image (s) by discriminant analysis, and a region having a higher signal value (s) than the threshold value is extracted as a lung field region candidate. Then, edge detection is performed on around the border of the extracted lung field region candidate, and, in small blocks around the border, points where the edge is the maximum are extracted along the border, so that the border of a lung field region can be extracted. Next, one of the frame images is determined as a reference image, and between the reference image and the other frame images, publically-known local matching and warping (described, for example, in Japanese Patent Application Publication No. 2012-5729) are performed so that position shift in the lung field regions between the frame images is corrected. The corrected lung field regions are extracted as the lung field regions of each frame image.

Next, the control unit 31 calculates the ventilation amount index value (Step S13).

In Step S13, first, for each frame image, a measure of central tendency (e.g., the mean, the median, etc.) of the pixel signal values of the extracted lung field region(s) is calculated, and the pixel signal values of the lung field region is replaced with the measure of central tendency. Next, time change in the pixel signal value (the measure of central tendency) of the lung field region is calculated, and the calculated time change is filtered with a low-pass filter (e.g., a cutoff frequency of 0.5 Hz) in the time direction. This removes signal change at high frequency due to perfusion and the like from the dynamic image, and accordingly can extract time change in signal value due to ventilation (low time-frequency component). Next, a difference value in the pixel signal value of the lung field region between adjacent frame images in terms of time in the selected analysis range of the dynamic image filtered with the low-pass filter is calculated. This frame-to-frame difference value is the ventilation amount index value.

Next, the control unit 31 calculates the perfusion amount index value (Step S14).

In Step S14, first, for each frame image, a measure of central tendency (e.g., the mean, the median, etc.) of the pixel signal values of the extracted lung field region(s) is calculated, and the pixel signal values of the lung field region is replaced with the measure of central tendency. Next, time change in the pixel signal value (the measure of central tendency) of the lung field region is calculated, and the calculated time change is filtered with a high-pass filter (e.g., a cutoff frequency of 0.7 Hz) in the time direction. This removes signal change at low frequency due to ventilation and the like from the dynamic image, and accordingly can extract time change in signal value due to perfusion (high time-frequency component). Although, a high-pass filter is used here to extract time change in the signal value due to perfusion, a band-pass filter to extract a particular frequency component(s) may be used instead. Next, a difference value in the pixel signal value of the lung field region between adjacent frame images in terms of time in the selected analysis range of the dynamic image filtered with the high-pass filter is calculated. This frame-to-frame difference value is the perfusion amount index value.

Next, the control unit 31 divides the calculated ventilation amount index value by the calculated perfusion amount index value, thereby calculating the V/Q ratio (Step S15). Here, the ratio of the ventilation amount index value to the perfusion amount index value calculated by using the same frame images is calculated.

Then, the control unit 31 displays the calculation results of the V/Q ratio on the display unit 34 (Step S16).

Needless to say, the optimum V/Q ratio can be calculated when the same frame images are used to calculate the ventilation amount index value and the perfusion amount index value. However, in the case of a dynamic image composed of a large number of frame images, even if the frame images used to calculate the ventilation amount index value and the frame images used to calculate the perfusion amount index value are different (including partly different) from each other by one or a few frame images in the time direction, the V/Q ratio calculated in this state is approximately the same as that calculated from the ventilation amount index value and the perfusion amount index value calculated by using the same frame images. This is because no large difference is generated in each index value between, for example, when each index value is calculated by using a first frame image and its adjacent second frame image and when each index value is calculated by using the second frame image and its adjacent third frame image. Thus, the above case causes no practical problem. Therefore, the above case is included in the scope of claims of the present application.

Figure 8A:
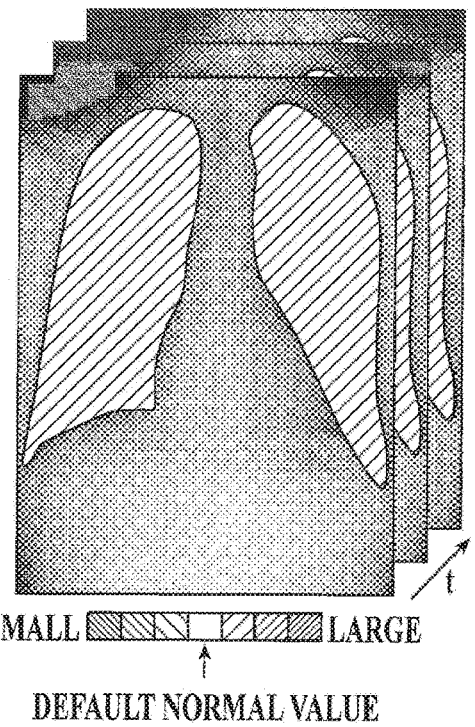
FIG. 8A shows an example of calculation results of the V/Q ratio in a first embodiment displayed in the form of a video.
Figure 8B:
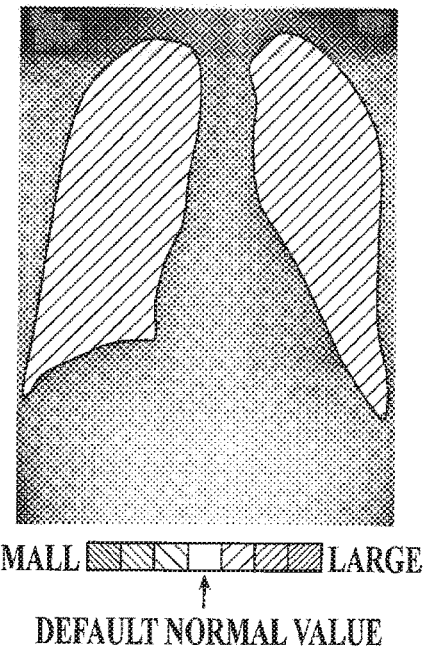
FIG. 8B shows an example of the calculation results of the V/Q ratio in the first embodiment displayed in the form of a still image.
Figure 9A:
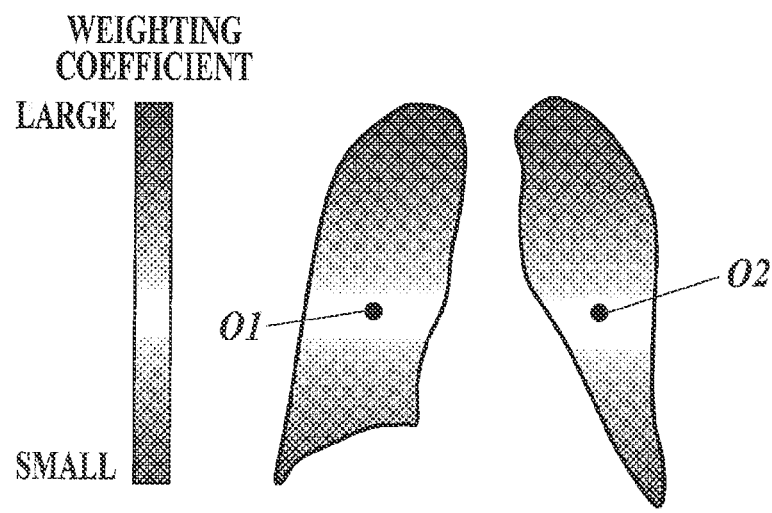
FIG. 9A shows a linear weighting coefficient by which a normal value is multiplied.
Figure 9B:
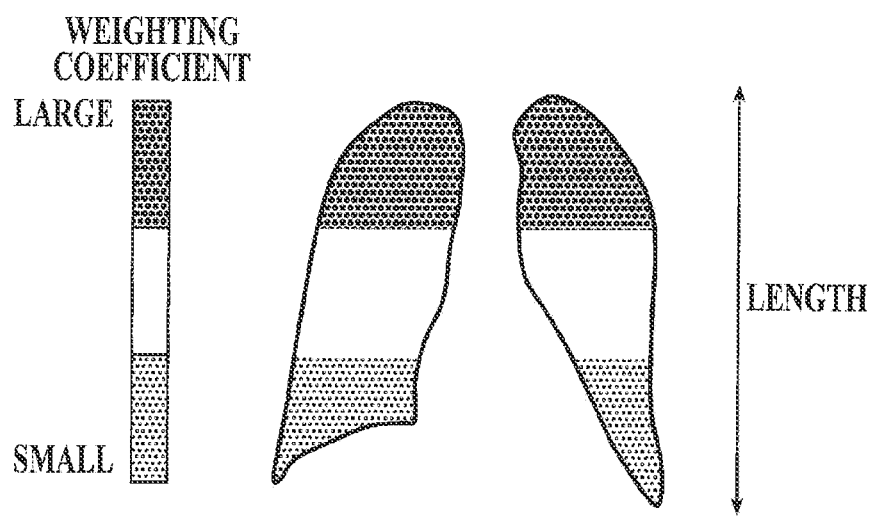
FIG. 9B shows a stepwise weighting coefficient by which the normal value is multiplied.

FIG. 8A and FIG. 8B show examples of the calculation results of the V/Q ratio displayed in Step S16. In Step S16, the control unit 31 may color the lung field regions of each frame image according to the value(s) of the calculation result (s) of the V/Q ratio, and display the colored frame images successively (as a video) as shown in FIG. 8A, or may calculate a measure(s) of central tendency of the V/Q ratio calculated from the frame images, color the lung field regions of one frame image according to the measure(s) of central tendency of the V/Q ratio, and display the colored frame image (as a still image) as shown in FIG. 8B. At the time, as shown in each of FIG. 8A and FIG. 8B, it is preferable to display an indicator showing a relationship between colors and values of the V/Q ratio. Further, if coloring according to the V/Q ratio is performed, it is preferable, for example, to compare the calculated V/Q ratio with a predetermined normal value and change the color according to the comparison result. This allows a user to recognize at a glance if there is an abnormality in the lung fields of an examinee. Further, if imaging is performed with an examinee standing, as described above, due to influence of gravity, the amount of ventilation tends to be more than the above value at the upper part of the lung fields, and the amount of perfusion tends to be more than the above value at the lower part thereof. Hence, as shown in FIG. 9A, the normal value may be weighted linearly from the respective centroids O1 and O2 of the right and left lung fields to the upper end and the lower end. Alternatively, as shown in FIG. 9B, three levels of the weight may be prepared for the upper part, the middle part and the lower part, respectively, into which the lung fields (i.e., the length thereof in the vertical direction) is equally divided. Using different normal values for respective parts of the lung fields enables evaluation of the V/Q ratio with influence of gravity or the like taken into account.

Displaying the calculation results of the V/Q ratio in the form of a video as shown in FIG. 8A allows a user to recognize change in the V/Q ratio due to breathing, whereas displaying the calculation results of the V/Q ratio by the measure(s) of central tendency, in which the calculation results are summarized, as shown in FIG. 8B allows a user to recognize tendency of the overall V/Q ratio during breathing.

Second Embodiment

Hereinafter, a second embodiment of the present invention is described.

The configurations (and components) and the imaging actions in the second embodiment are the same as those described in the first embodiment. Therefore, the descriptions thereof are not repeated here, and actions of the diagnostic console 3 in the second embodiment are described.

In the diagnostic console 3, when receiving a series of frame images of a dynamic image from the imaging console 2 through the communication unit 35, the control unit 31 performs a V/Q ratio calculation process B shown in FIG. 10 in cooperation with the program stored in the storage unit 32.

FIG. 10 is a flowchart of the V/Q ratio calculation process B performed by the control unit 31 of the diagnostic console 3 in the second embodiment.

First, the control unit 31 selects an analysis range from a series of frame images of a dynamic image (Step S21). Selection of the analysis range in Step S21 is the same as that in Step S11, and therefore the description thereof is not repeated here.

Next, the control unit 31 extracts the lung field regions from each frame image of the selected analysis range (frame images) of the dynamic image (Step S22).

Next, the control unit 31 divides the extracted lung field regions into small regions (Step S23).

In Step S23, for example, first, one of the frame images is determined as a reference image, and the lung field regions of the reference image are divided into small regions (square regions) each having a predetermined size (e.g., 0.4 to 4 cm square). As the reference image, a frame image at the resting expiratory level having the minimum area of the lung field regions is preferable. This is because if such a frame image is used as the reference image, when the small regions of the reference image are correlated with each of the other frame images, the small regions are not correlated with the outside of the lung field regions of each of the other frame images. Next, in each of the other frame images, small regions are set at the regions composed of pixels corresponding to the pixels of the small regions set in the reference image (i.e., set at the regions having signal values output from the detection elements of the radiation detection unit 13, used for imaging, from which the signal values of the small regions set in the reference image have been output), and the corresponding small regions of the frame images are correlated with each other. These division into small regions and correlation may be performed after publically-known local matching and warping (described, for example, in Japanese Patent Application Publication No. 2012-5729) are performed so that position shift in the lung field regions between the frame images is corrected.

Next, the control unit 31 calculates, for each small region, the ventilation amount index value (Step S24).

In Step S24, first, for each small region of each frame image, a measure of central tendency (e.g., the mean, the median, etc.) of the pixel signal values of the small region is calculated, and the pixel signal values of the small region is replaced with the measure of central tendency. Next, for each small region, time change in the pixel signal value (the measure of central tendency) is calculated, and the calculated time change is filtered with a low-pass filter (e.g., a cutoff frequency of 0.5 Hz) in the time direction. This removes, in each small region, signal change at high frequency due to perfusion and the like, and accordingly can extract time change in signal value due to ventilation (low time-frequency component). Next, for each small region, a difference value in the pixel signal value of the lung field region between adjacent frame images in terms of time in the selected analysis range of the dynamic image filtered with the low-pass filter is calculated. This frame-to-frame difference value is the ventilation amount index value for the small region.

Next, the control unit 31 calculates, for each small region, the perfusion amount index value (Step S25).

In Step S25, first, for each small region of each frame image, a measure of central tendency (e.g., the mean, the median, etc.) of the pixel signal values of the small region is calculated, and the pixel signal values of the small region is replaced with the measure of central tendency. Next, for each small region, time change in the pixel signal value (the measure of central tendency) is calculated, and the calculated time change is filtered with a high-pass filter (e.g., a cutoff frequency of 0.7 Hz) in the time direction. This removes, in each small region, signal change at low frequency due to ventilation and the like, and accordingly can extract time change in signal value due to perfusion (high time-frequency component). Although a high-pass filter is used here to extract time change in signal value due to perfusion, a band-pass filter to extract a particular frequency component(s) may be used instead. In this case, filtering is performed with a lower cutoff frequency of 0.7 Hz and an upper cutoff frequency of 2.4 Hz. Next, for each small region, a difference value in the pixel signal value of the lung field region between adjacent frame images in terms of time in the selected analysis range of the dynamic image filtered with the high-pass filter is calculated. This frame-to-frame difference value is the perfusion amount index value for the small region.

Next, for each small region, the control unit 31 divides the calculated ventilation amount index value by the calculated perfusion amount index value, thereby calculating the V/Q ratio (Step S26).

Then, the control unit 31 displays the calculation results of the V/Q ratio on the display unit 34 (Step S27).

Figure 11A:
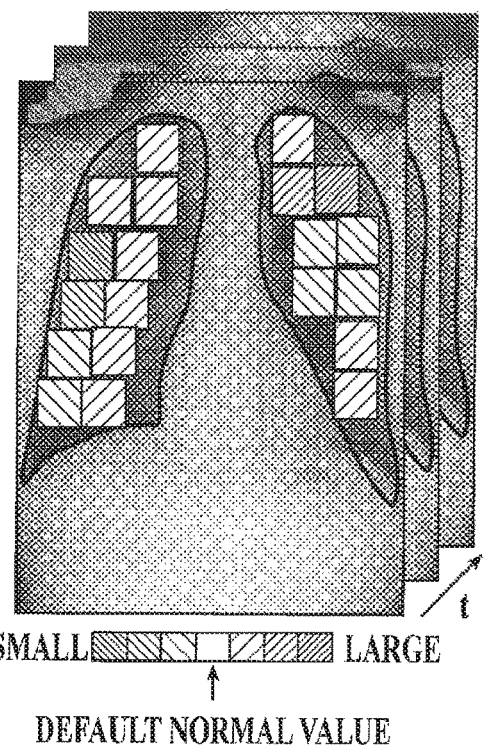
FIG. 11A shows an example of calculation results of the V/Q ratio in a second embodiment displayed in the form of a video.
Figure 11B:
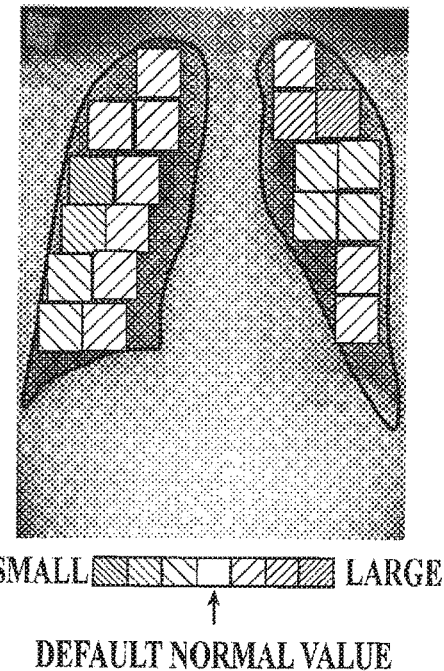
FIG. 11B shows an example of the calculation results of the V/Q ratio in the second embodiment displayed in the form of a still image.

FIG. 11A and FIG. 11B show examples of the calculation results of the V/Q ratio displayed in Step S27. In Step S27, the control unit 31 may color each small region (of the lung field regions) of each frame image according to the value of the calculation result of the V/Q ratio, and display the colored frame images successively (as a video) as shown in FIG. 11A, or may calculate, for each small region, a measure of central tendency of the calculation results of the V/Q ratio calculated from the frame images, color each small region (of the lung field regions) of one frame image according to the measure of central tendency of the V/Q ratio, and display the colored frame image (as a still image) as shown in FIG. 11B. At the time, as shown in each of FIG. 11A and FIG. 11B, it is preferable to display an indicator showing a relationship between colors and values of the V/Q ratio. Coloring and weighting in the second embodiment are the same as those described in the first embodiment, and therefore the descriptions thereof are not repeated here.

Calculating the V/Q ratio for each small region and displaying the calculation results in the form of a video as shown in FIG. 11A allows a user to recognize change in the V/Q ratio of each local region of the lung field regions due to breathing, whereas calculating, for each small region, a measure of central tendency of the calculation results of the V/Q ratio calculated from the frame images and displaying the calculation results of the V/Q ratio of each small region by the measure of central tendency, in which the calculation results of the small region are summarized, as shown in FIG. 11B allows a user to recognize tendency of the V/Q ratio of each local region of the lung field regions. Further, comparing the V/Q ratio with a predetermined normal value, coloring each small region of each frame image or one frame image according to the comparison result and displaying the colored frame images or frame image allows a user to recognize at a glance if there is an abnormality in the lung fields of an examinee. Further, using different normal values for respective parts of the lung fields enables evaluation of the V/Q ratio with influence of gravity or the like taken into account.

As described above, according to the diagnostic console 3, the control unit 31: selects an analysis range (a first plurality of frame images to be analyzed) from a series of frame images showing the dynamic state of a chest part; calculates, based on the analysis range (the first plurality of frame images), the ventilation amount index value, which indicates the amount of ventilation of a lung field(s), and the perfusion amount index value, which indicates the amount of perfusion of the lung field; and calculates the ratio of the ventilation amount index value to the perfusion amount index value. If selecting, from the series of frame images showing the dynamic state of the chest part, an analysis range (a second plurality of frame images to be analyzed) as to the ventilation function of the lung field and an analysis range (a third plurality of frame images to be analyzed) as to the perfusion function of the lung field, the control unit 31 selects, as the above analysis range (the first plurality of frame images), overlapping frame images of the analysis ranges (the second plurality of frame images and the third plurality of frame images).

Thus, the control unit 31 calculates the ventilation amount index value and the perfusion amount index value based on the frame images of the same analysis range. Therefore, the V/Q ratio can be calculated with higher accuracy than ever before.

Further, the control unit 31 calculates the ratio of the ventilation amount index value to the perfusion amount index value (the V/Q ratio) calculated by using the same frame images. Therefore, the V/Q ratio can be calculated with higher accuracy than ever before.

Further, the control unit 31 divides a lung field region(s) of the first plurality of frame images into small regions, and calculates the V/Q ratio for each of the small regions. Therefore, local V/Q ratio information about the lung fields can be provided.

Further, the control unit 31 filters, with a low-pass filter in the time direction, time change in pixel signal value of (a) a lung field region of the first plurality of frame images or (b) each of small regions into which the lung field region of the first plurality of frame images is divided; and calculates, for the whole lung field region or each of the small regions of each of the first plurality of frame images, the ventilation amount index value based on the pixel signal value of the lung field region or each of the small regions of the first plurality of frame images filtered with the low-pass filter. The control unit 30 also filters, with a high-pass filter or band-pass filter in the time direction, time change in pixel signal value of the lung field region or each of the small regions of the first plurality of frame images; and calculates, for the whole lung field region or each of the small regions of each of the first plurality of frame images, the perfusion amount index value based on the pixel signal value of the lung field region or each of the small regions of the first plurality of frame images filtered with the high-pass filter. Then, the control unit 31 calculates the V/Q ratio for the whole lung field region or each of the small regions. Therefore, the ventilation amount index value and the perfusion amount index value can be calculated with high accuracy, and accordingly the V/Q ratio can be calculated with high accuracy.

Further, the control unit 31 displays the calculation result(s) of the V/Q ratio on the display unit 34. Therefore, a user can see and check the V/Q ratio. For example, the control unit 31 compares the calculation result of the V/Q ratio with a predetermined normal value, colors each of the first plurality of frame images (or one frame image) according to the comparison result, and displays, as the calculation result, the colored first plurality of frame images (or one frame image) on the display unit 34. Therefore, a user can recognize at a glance if there is an abnormality in the lung fields of an examinee. Further, the normal value to be used differs according to the part of the lung field(s). Therefore, the value of the V/Q ratio can be evaluated with influence of gravity or the like taken into account.

Those described in the above are preferred examples of the dynamic analysis system of the present invention, and not intended to limit the present invention.

For example, in the above, the ventilation amount index value and the perfusion amount index value are calculated by filtering time change in pixel signal value of a dynamic image with frequency filters in the time direction, and thereafter calculating the frame-to-frame difference values. However, the calculation methods of the ventilation amount index value and the perfusion amount index value are not limited thereto.

Further, in the above, a hard disk, a nonvolatile semiconductor memory or the like is used as a computer readable medium of the programs of the present invention. However, this is not a limitation. As the computer readable medium, a portable storage medium, such as a CD-ROM, can also be used. Further, as a medium to provide data of the programs of the present invention, a carrier wave can be used.

In addition to the above, detailed configurations and detailed actions of the devices or the like of the dynamic analysis system 100 can also be appropriately modified without departing from the spirit of the present invention.

What is claimed is:

1. A dynamic analysis system comprising:
an imaging device which performs dynamic imaging by emitting radiation to a chest part of a human body, thereby obtaining a series of frame images showing a dynamic state of the chest part; and
an analysis device including a controller which:
selects a first plurality of frame images to be analyzed from the series of frame images obtained by the imaging device;
calculates, based on the first plurality of frame images, a ventilation amount index value that indicates an amount of ventilation of a lung field and a perfusion amount index value that indicates an amount of perfusion of the lung field; and
calculates a ratio of the ventilation amount index value to the perfusion amount index value,
wherein the controller:
filters, with a low-pass filter in a time direction, time change in pixel signal value of (a) a lung field region of the first plurality of frame images or (b) each of small regions into which the lung field region of the first plurality of frame images is divided;
calculates, for the whole lung field region or each of the small regions of each of the first plurality of frame images, the ventilation amount index value based on the pixel signal value of the lung field region or each of the small regions of the first plurality of frame images filtered with the low-pass filter;
filters, with a high-pass filter or band-pass filter in the time direction, the time change in the pixel signal value of the lung field region or each of the small regions of the first plurality of frame images; and
calculates, for the whole lung field region or each of the small regions of each of the first plurality of frame images, the perfusion amount index value based on the pixel signal value of the lung field region or each of the small regions of the first plurality of frame images filtered with the high-pass filter.

2. The dynamic analysis system according to claim 1, wherein the controller:
selects, from the series of frame images, a second plurality of frame images to be analyzed as to a ventilation function of the lung field and a third plurality of frame images to be analyzed as to a perfusion function of the lung field; and
selects, as the first plurality of frame images, overlapping frame images of the second plurality of frame images and the third plurality of frame images.

3. The dynamic analysis system according to claim 1, wherein the controller calculates the ratio of the ventilation amount index value to the perfusion amount index value calculated by using, of the first plurality of frame images, same frame images as frame images used to calculate the ventilation amount index value.

4. The dynamic analysis system according to claim 1, wherein the controller:
divides a lung field region of the first plurality of frame images into small regions; and
for each of the small regions,
calculates the ventilation amount index value and the perfusion amount index value, and calculates the ratio of the ventilation amount index value to the perfusion amount index value.

5. The dynamic analysis system according to claim 1, wherein
the analysis device further includes a display which displays thumbnail images of the series of frame images, and
the controller selects the first plurality of frame images based on frame images specified through a user operation from the thumbnail images displayed on the display.

6. The dynamic analysis system according to claim 1, wherein
the analysis device further includes a display which displays a waveform showing time change in pixel signal value of a whole image in the series of frame images, and
the controller selects the first plurality of frame images based on a range specified through a user operation with respect to the waveform displayed on the display.

7. The dynamic analysis system according to claim 1, wherein
the analysis device further includes a display which displays a waveform showing time change in diaphragm position in the series of frame images, and
the controller selects the first plurality of frame images based on a range specified through a user operation with respect to the waveform displayed on the display.

8. The dynamic analysis system according to claim 1, wherein the controller automatically selects the first plurality of frame images based on time change in pixel signal value of a whole image in the series of frame images.

9. The dynamic analysis system according to claim 1, wherein the controller automatically selects the first plurality of frame images based on respiratory guidance information at a time of the imaging associated with each of the series of frame images.

10. The dynamic analysis system according to claim 1, wherein the analysis device further includes a display which displays a calculation result of the ratio of the ventilation amount index value to the perfusion amount index value.

11. The dynamic analysis system according to claim 10, wherein the display displays the calculation result in a form of a video.

12. The dynamic analysis system according to claim 10, wherein the controller:
compares the calculation result with a predetermined normal value, thereby obtaining a comparison result;
colors each of the first plurality of frame images according to the comparison result; and
displays, as the calculation result, the colored first plurality of frame images on the display.

13. The dynamic analysis system according to claim 12, wherein the normal value differs according to a part of the lung field.

14. An analysis device comprising a controller which:
selects a plurality of frame images to be analyzed from a series of frame images showing a dynamic state of a chest part of a human body obtained by dynamic imaging performed by emitting radiation to the chest part of the human body;
calculates, based on the selected plurality of frame images, a ventilation amount index value that indicates an amount of ventilation of a lung field and a perfusion amount index value that indicates an amount of perfusion of the lung field;

calculates a ratio of the ventilation amount index value to the perfusion amount index value;

filters, with a low-pass filter in a time direction, time change in pixel signal value of (a) a lung field region of the first plurality of frame images or (b) each of small regions into which the lung field region of the first plurality of frame images is divided;

calculates, for the whole lung field region or each of the small regions of each of the first plurality of frame images, the ventilation amount index value based on the pixel signal value of the lung field region or each of the small regions of the first plurality of frame images filtered with the low-pass filter;

filters, with a high-pass filter or band-pass filter in the time direction, the time change in the pixel signal value of the lung field region or each of the small regions of the first plurality of frame images; and calculates, for the whole lung field region or each of the small regions of each of the first plurality of frame images, the perfusion amount index value based on the pixel signal value of the lung field region or each of the small regions of the first plurality of frame images filtered with the high-pass filter.

* * * * *